United States Patent
Mahajan et al.

(10) Patent No.: US 7,951,144 B2
(45) Date of Patent: May 31, 2011

(54) THERMAL AND ELECTRICAL CONDUCTIVITY PROBES AND METHODS OF MAKING THE SAME

(76) Inventors: Roop L. Mahajan, Blacksburg, VA (US); Ming Yi, Blacksburg, VA (US); Ronald J. Podhajsky, Boulder, CO (US); Hrishikesh V. Panchawagh, Rochester, NY (US)

( * ) Notice: Subject to any disclaimer, the term of this patent is extended or adjusted under 35 U.S.C. 154(b) by 597 days.

(21) Appl. No.: 12/016,754

(22) Filed: Jan. 18, 2008

(65) Prior Publication Data
US 2008/0175299 A1    Jul. 24, 2008

Related U.S. Application Data

(60) Provisional application No. 60/881,238, filed on Jan. 19, 2007.

(51) Int. Cl.
*A61B 18/18* (2006.01)
*G01N 25/00* (2006.01)
*G01N 25/18* (2006.01)
*G01N 25/20* (2006.01)

(52) U.S. Cl. ............... 606/41; 374/10; 374/11; 374/43; 374/44

(58) Field of Classification Search ............. 374/10–11, 374/43–44; 606/41
See application file for complete search history.

(56) References Cited

U.S. PATENT DOCUMENTS

| | | | |
|---|---|---|---|
| 4,038,975 A | 8/1977 | Vrana et al. | |
| 4,291,708 A | 9/1981 | Frei et al. | |
| 4,537,203 A | 8/1985 | Machida | |
| 4,617,939 A | 10/1986 | Brown et al. | |
| 4,719,441 A | 1/1988 | Horn | |
| 4,729,385 A | 3/1988 | Juncosa et al. | |
| 4,955,383 A | 9/1990 | Faupel | |
| 4,960,109 A * | 10/1990 | Lele ...................... | 374/E13.002 |
| 4,966,158 A | 10/1990 | Honma et al. | |
| 5,035,514 A * | 7/1991 | Newman ...................... | 374/135 |
| 5,184,620 A | 2/1993 | Cudahy et al. | |
| 5,184,624 A | 2/1993 | Brown et al. | |
| 5,217,014 A | 6/1993 | Hahn et al. | |
| 5,320,101 A | 6/1994 | Faupel et al. | |
| 5,353,802 A | 10/1994 | Ollman | |
| 5,630,426 A | 5/1997 | Eggers et al. | |
| 5,704,355 A | 1/1998 | Bridges | |
| 5,800,350 A | 9/1998 | Coppleson et al. | |
| 6,026,323 A | 2/2000 | Skladnev et al. | |
| 6,190,378 B1 * | 2/2001 | Jarvinen ........................ | 606/21 |
| 6,845,264 B1 | 1/2005 | Skladnev et al. | |

(Continued)

FOREIGN PATENT DOCUMENTS

DE    3711511    6/1988

(Continued)

OTHER PUBLICATIONS

U.S. Appl. No. 12/016,761, Podhajsky.

*Primary Examiner* — Lisa M Caputo
*Assistant Examiner* — Jonathan Dunlap

(57) ABSTRACT

According to the present disclosure, a system for sensing attributes of tissue in at least one direction is provided. The system includes a thermal conductivity probe having a sensor configured to measure thermal conductivity in the target tissue in at least one direction, and an electrical conductivity probe having a sensor configured to measure electrical conductivity in the target tissue in at least one direction, a power supply operatively coupled to the thermal conductivity probe and being configured to supply power to the thermal conductivity probe, an impedance analyzer operatively coupled to the electrical conductivity probe, and a computer operatively coupled to at least one of the power supply, the multimeter and the impedance analyzer.

16 Claims, 7 Drawing Sheets

U.S. PATENT DOCUMENTS

| | | | |
|---|---|---|---|
| 2002/0173731 A1* | 11/2002 | Martin et al. | 600/549 |
| 2003/0097130 A1* | 5/2003 | Muller et al. | 606/41 |
| 2004/0015162 A1 | 1/2004 | McGaffigan | |
| 2004/0037343 A1* | 2/2004 | Tanaka et al. | 374/31 |
| 2005/0090881 A1* | 4/2005 | Frank et al. | 607/105 |
| 2007/0049915 A1* | 3/2007 | Haemmerich et al. | 606/32 |
| 2007/0060921 A1* | 3/2007 | Janssen et al. | 606/41 |
| 2008/0025366 A1* | 1/2008 | McBurney | 374/44 |
| 2008/0161797 A1* | 7/2008 | Wang et al. | 606/41 |

FOREIGN PATENT DOCUMENTS

| | | |
|---|---|---|
| DE | 102004022206 | 12/2005 |
| DE | 202005015147 | 2/2006 |
| EP | 0558429 | 9/1993 |
| WO | WO 9944520 | 9/1999 |
| WO | WO 0054682 | 9/2000 |
| WO | WO 0070333 | 11/2000 |
| WO | WO 2004052182 | 6/2004 |

\* cited by examiner

THERMAL AND ELECTRICAL CONDUCTIVITY PROBES AND METHODS OF MAKING THE SAME

CROSS-REFERENCE TO RELATED APPLICATION

The present application claims the benefit of and priority to U.S. Provisional Application Ser. No. 60/881,238, filed on Jan. 19, 2007, the entire content of which is incorporated herein by reference.

BACKGROUND

1. Technical Field

The present disclosure relates to electrosurgical instruments, systems and methods of making the same. More particularly, the present disclosure relates to conductivity probes for sensing directional attributes of tissue and methods of making the same.

2. Discussion of Related Art

It has been observed that biological tissue has different thermal and/or electrical conductivities in different directions.

Thermal conductivity of biological tissues is dependent on the particular type of biological tissue and on the composition of the biological tissue. Different biological tissues exhibit different and/or unique thermal conductivity based on factors such as tissue density, vascularization, age, direction and distance to major blood vessels, etc. Additionally, different biological tissues may exhibit a different and/or unique thermal conductivity in different directions.

Electrical conductivity is not only determined by tissue type and composition, but also by other externally applied physical and chemical influences during thermal treatment, such as, for example, temperature inducement and saline pretreatment.

Knowing the thermal and/or electrical conductivity of tissue may be used by a surgeon in a number of applications, including, but not limited to, predicting the effect of thermal treatment on given tissue, identifying the location and size of internal structures, and enhancing the resolution of traditional imaging devices.

SUMMARY

Accordingly, a need exists for thermal and electrical conductivity probes for sensing the directional attributes of tissue and methods of making the same.

A system for sensing attributes of tissue in at least one direction is provided. The system includes a thermal conductivity probe including a sensor configured to measure thermal conductivity in the target tissue in at least one direction, a power supply operatively connected to the thermal conductivity probe and being configured to supply power to the thermal conductivity probe, a multimeter operatively connected the thermal conductivity probe; an electrical conductivity probe including a sensor configured to measure electrical conductivity in the target tissue in at least one direction, an impedance analyzer to measure the tissue impedance (or equivalently electrical conductivity) and a computer operatively connected to at least one of the multimeter and impedance analyzer. In the system, the thermal conductivity probe and the electrical conductivity probe may be integrated into a single probe.

Also provided is a thermal conductivity probe for sensing directional attributes of tissue. The probe includes a body and a sensor operably connected to the body. The sensor includes a line heater having one or more resistive heating elements, a detector having one or more detector elements, and a substrate for supporting the line heater and the detector and to provide thermal conductivity contrast. The body of the probe may define a catheter configured for insertion into tissue. The pair of outer detector elements may form resistance temperature detector elements (RTD). The pair of inner heating elements may be substantially parallel. The probe may further include an array of sensors.

A method of making a thermal conductivity probe is also provided. The method includes providing an inert substrate, depositing a first layer on the substrate, depositing a second layer on the first layer, generating a first pattern in the first and second layers, generating a second pattern in the second layer, and depositing an insulative layer over the first and second layers. The first and second layers may be deposited using evaporation techniques. The first layer may be selected from the group consisting of titanium (Ti), titanium tungsten (TiW) and platinum (Pt). The second layer may be selected from the group consisting of gold (AU), iridium (Ir) and platinum-iridium (Pt—Ir). The first layer may measure about 50 nm thick. The second layer may measure about 500 nm thick. The first and second patterns may be generated using an etching technique.

In addition, an electrical conductivity probe for measuring attributes of tissue is provided. The probe includes a body and a sensor for sensing electrical conductivity. The sensor includes a pair of electrodes, a pair of bonding pads coupled to the pair of electrodes by a pair of electrical leads, and a substrate for supporting the electrodes, boding pads and leads. The pair of electrodes may be parallel. The body of the probe may define a catheter configured for insertion into tissue.

The sensor may include insulating material at least partially overlying the pair of electrodes, and an exposed region formed in the insulation and associated with each electrode.

A method of making an electrical conductivity probe is also provided. The method includes providing a substrate, depositing an adhesive layer on the substrate, depositing a conductive layer on the adhesive layer, generating a pattern on the adhesive layer and the conductive layer, and depositing an insulating layer over the conductive layer and the pattern. The adhesive layer and conductive layer may be deposited using evaporation techniques. The pattern may define first and second electrodes. The adhesive layer may be selected from the group consisting of titanium (Ti), titanium tungsten (TiW) and platinum (Pt), and may measure about 30 nm thick. The conductive layer selected from the group consisting of gold (AU), iridium (Ir) and platinum-iridium (Pt—Ir), and may measure about 330 nm thick. The insulative layer may be spun onto the conductive layer and pattern.

DETAILED DESCRIPTION OF THE DRAWINGS

Embodiments of the present disclosure are disclosed herein with reference to the drawings, wherein.

DETAILED DESCRIPTION OF EMBODIMENTS

Figure 1:
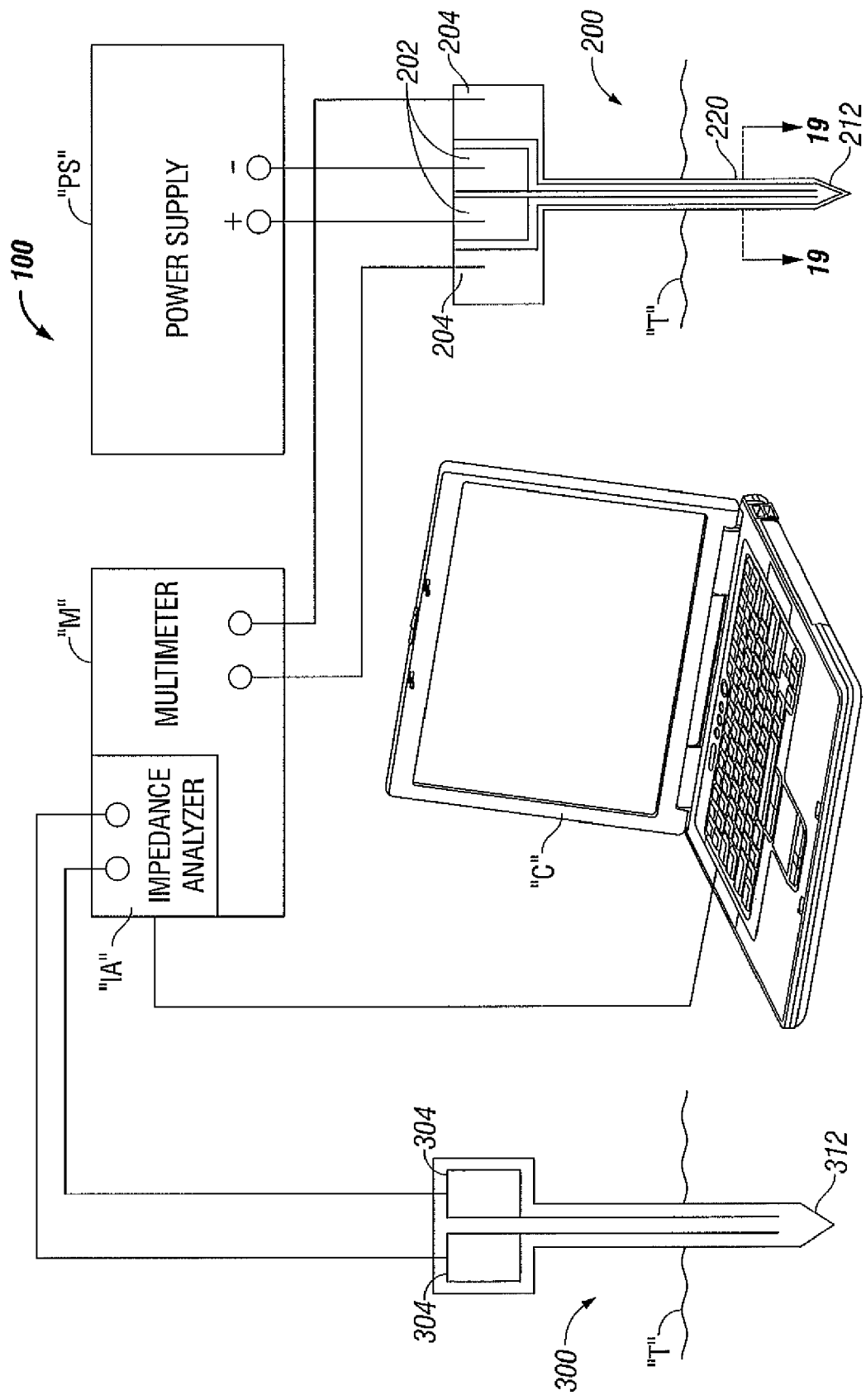
FIG. 1 is a schematic perspective view of a sensing system according to an embodiment of the present disclosure.

The devices, systems and methods of the present disclosure provide for the sensing of directional attributes of tissue in order to help in predicting and/or planning thermal therapy procedures. In the drawings and in the description which follows, the term "proximal", as is traditional, will refer to the end of the system, or component thereof which is closest to the operator, and the term "distal" will refer to the end of the system, or component thereof, which is more remote from the operator.

As used herein, the term "thermal treatment" is understood to include and is not limited to radio-frequency (RF) treatment, laser treatment, microwave treatment and cryoablation treatment.

1. Sensing System

With reference to FIG. 1, in accordance with an embodiment of the present disclosure, a sensing system for sensing directional attributes of tissue is generally designated as 100. System 100 includes a thermal conductivity probe 200, power supply "PS" connected to or connectable to probe 200, a multimeter "M" connected to or connectable to probe 200, and a computer "C" connected to or connectable to multimeter "M". System 100 may further include an electrical conductivity probe 300 connected to an impedance analyzer "IA", or other suitable devices. Impedance analyzer "IA" may be formed integral with multimeter "M", or may instead include a separate unit. Power supply "PS" may include any power source capable of providing constant power. For example, power supply "PS" may include a DC power source.

As seen in FIG. 1, thermal conductivity probe 200 includes a first pair of bonding pads 202 electrically connected to or electrically connectable to power supply "PS", and a second pair of bonding pads 204 electrically connected to or electrically connectable to multimeter "M". Electrical conductivity probe 300 may include a pair of bonding pads 304 electrically connected to or electrically connectable to impedance analyzer "IA".

2. Thermal Conductivity Probe

A micro thin-film thermal conductivity probe has been developed to measure thermal conductivity of biological tissues based on the principle of traditional hot-wire method. An embodiment of the design of the microprobe of the present disclosure includes a resistive line heating element on a substrate and a Resistance Temperature Detector (RTD) based temperature sensor.

Figure 2A:
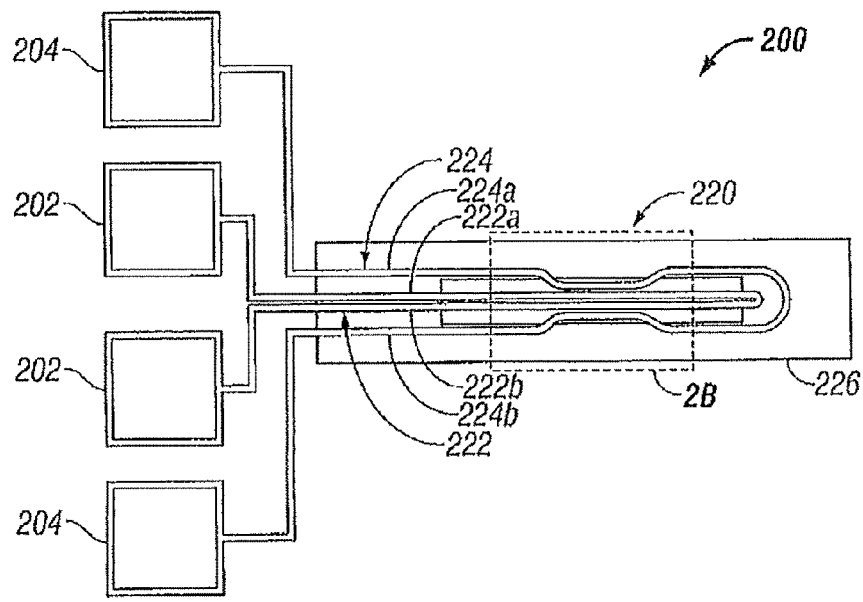
FIG. 2A is a schematic illustration of an embodiment of a micro thermal probe of the sensing system of FIG. 1.
Figure 2B:
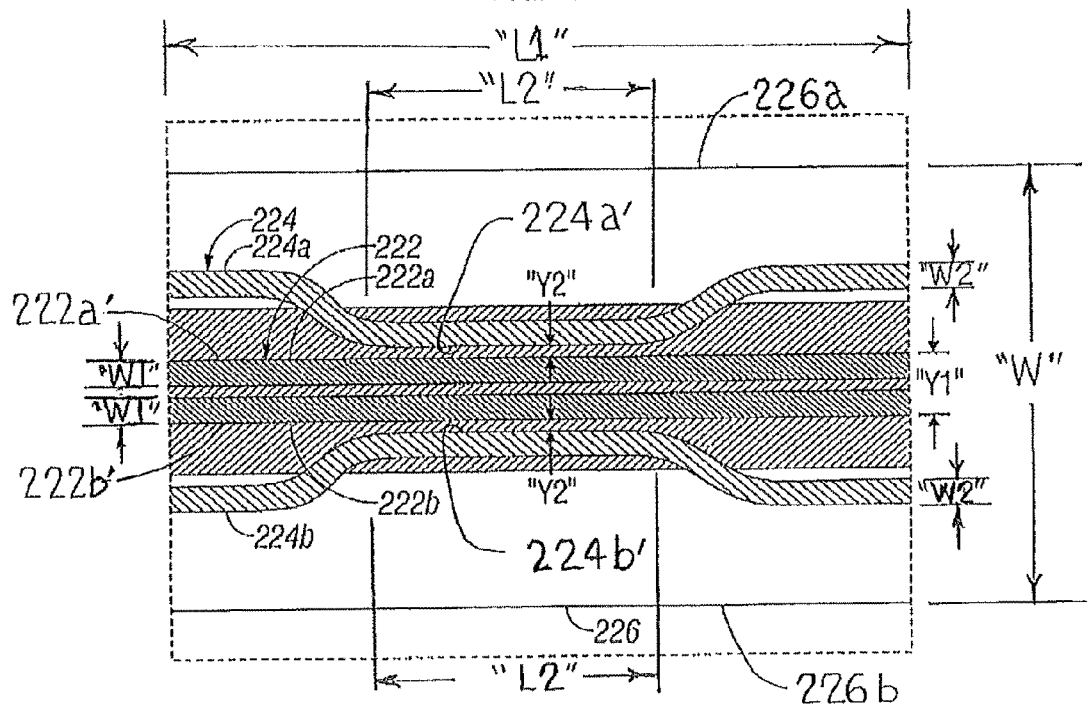
FIG. 2B is an enlarged view of the indicated area of detail of FIGS. 2A and 2B.

With continued reference to FIG. 1 and with reference to FIGS. 2A and 2B, a more detailed discussion of thermal conductivity probe 200 is provided. Probe 200 may be in the form of a needle, probe antenna or the like or any other suitable configuration. In one embodiment, probe 200 may include an elongate body 210, in the form of a catheter, defining a sharpened or pointed distal tip 212.

Probe 200 further includes a microprobe sensor 220 suitably secured to catheter 210. Microprobe sensor 220 may be disposed at least partially within catheter 210, on an outer surface of catheter 210, imbedded in the outer surface of catheter 210 and/or according to any other suitable method.

As seen in FIGS. 2A and 2B, microprobe sensor 220 includes a line heating element 222 having a pair of resistive inner thin-film heating elements 222a, 222b, a detector element 224 having a pair of outer "resistance temperature detector" (RTD) elements 224a, 224b, and a substrate 226 for supporting heating elements 222a, 222b and RTD elements 224a, 224b. The substrate 226 defines a first lateral edge 226a and a second lateral edge 226b and defines a width "W" between the first lateral edge 226a and the second lateral edge 226b.

In one embodiment, line heating element 222 has a width "W1" of approximately 100 μm and a length "L1" of approximately 5000 microns (μm). Meanwhile, detector element 224 may have a width "W2" of approximately 100 μm and a length "L2" of approximately 1500 μm. The dimensions disclosed herein are representative, it is envisioned and within the scope of the present disclosure for the dimensions to have any suitable value, such as, for example, having lengths "L1", "L2" that are approximately 3.0 times greater than the lengths specified or having lengths that are approximately 0.2 times less than the lengths specified. The width "W" of the substrate 226 is greater than the widths "W1" and "W2". It is contemplated that the lengths selected, for example, may be chosen for optimal use in a specific target tissue, e.g., liver, lung, kidney, muscle, etc.

As best seen in FIG. 2B, heating elements 222a, 222b of line heating element 222 are substantially parallel to one another and are spaced a distance "Y1" from one another. Distance "Y1" may be approximately 100 μm. The first and second resistive heating elements 222a and 222b are disposed between the first and second detector elements 224a and 224b, respectively. Each heating element 222a, 222b is spaced apart from a respective RTD element 224a, 224b by a distance "Y2". The first and second detector elements 224a and 224b are disposed on the substrate substantially parallel to one another and each define an inner edge 224a' and 224b', respectively, along the length of the substrate 226. The first and second resistive heating elements 222a and 222b are disposed on the substrate substantially parallel to one another and each define an outer edge 222a' and 222b', respectively, along the length of the substrate 226. The first and second detector elements 224a and 224b are each disposed separately in an outer position with respect to, and closer to, the first and second lateral edges 226a, 226b defined by the substrate 226 as compared to the first and second resistive heating elements 222a, 222b, respectively. The first and second resistive heating elements 222a, 222b are each disposed separately in an inner position as compared to the first and second detector elements 224a, 224b and with respect to the first and second lateral edges 226a, 226b defined by the substrate 226, respectively. The first and second resistive heating elements 222a, 222b define the first width dimension "Y1" that characterizes the combined width of the first and second resistive heating elements 222a, 222b on the substrate 226 that is less than the second width dimension "W" defined by the distance between the first and second lateral edges 226a, 226b defined by the substrate 226. The distance "Y2" between the outer edges 222a', 222b' of the resistive heating elements 222a, 222b and the inner edges 224a', 224b' of the detector elements 224a, 224b each define a third width dimension that is distance "Y2". Distance "Y2" may be approximately 50 µm.

Figure 3:
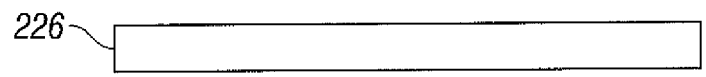
FIGS. 3-9 are schematic illustrations of exemplary steps in the fabrication of the micro thermal probe of FIG. 2.
Figure 4:
Figure 5:
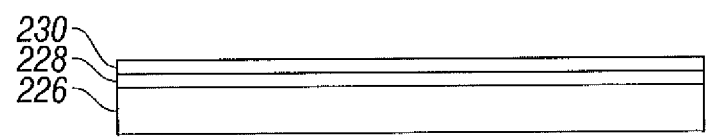

Turning now to FIGS. 3-9, a representative method of manufacturing microprobe sensor 220 is shown and described. The steps involved in the manufacture of microprobe sensor 220 include, as seen in FIG. 3, providing a substrate 226, e.g., glass, polyimide (kapton) or other polymeric substrate that is inert. In an embodiment, substrate 226 may have a thickness approximately equal to 1.0 mm. Next, as seen in FIG. 4, a first layer 228 is deposited on substrate 226 using evaporation techniques or other suitable deposition techniques. First layer 228 may be fabricated from titanium (Ti) titanium tungsten (TiW), platinum (Pt) or other like materials, and may have a thickness of approximately 50 nm. Next, as seen in FIG. 5, a second layer 230 is deposited on first layer 228 using evaporation techniques or other suitable deposition techniques. Second layer 230 may be fabricated from gold (Au), iridium (Ir), platinum-iridium alloy (Pt—Ir) or other like materials, and may have a thickness of approximately 500 nm. The dimensions of microprobe sensor 220 provided herein are merely representative, and may be made larger or smaller depending on the application. For example, microprobe sensor 220 may be reduced in size when configured for use with infants. In one exemplary embodiment, microprobe sensor 220 may include a substrate 226 having a thickness approximately equal to 300 µm to 1000 µm, and in a further embodiment approximately equal to 500 µm.

Figure 6:
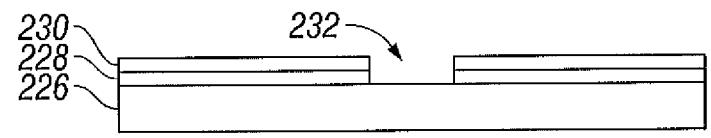
Figure 7:
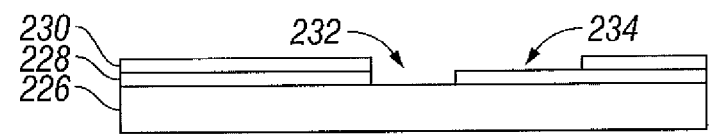

As seen in FIG. 6, suitable photolithography techniques or other suitable etching or removal techniques are used to generate a desired first pattern 232 in first and second layers 228, 230 by using a precision photomask (not shown). Next, as seen in FIG. 7, second layer 230 is etched, using photolithography techniques or other suitable etching or removal techniques, to create a second pattern 234 therein. In this manner, the heating elements and the RTD elements are defined.

Figure 8:
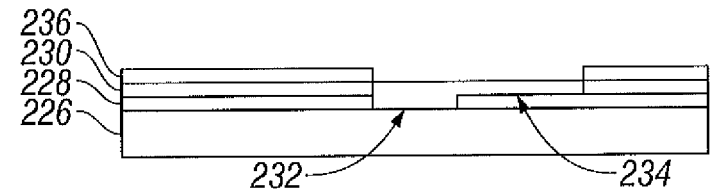
Figure 9:
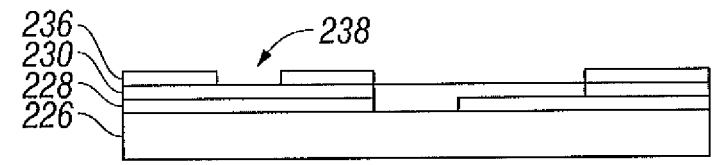

As seen in FIG. 8, an insulating layer 236 is deposited, i.e., spun onto, overtop first and second layers 228, 230 and first and second patterns 232, 234. Insulating layer 236 may comprise a dielectric layer of benzocyclobutane (BCB), silica (SiO2), parylene, polyimide, SU8, or other like materials. Insulating layer 236 functions to protect first and second layers 228, 230 from corrosive element in tissue, such as, for example, saline. As seen in FIG. 9, areas 238 are exposed in insulating layer 236 to define bonding pads 202, 204 and expose bonding pads 202, 204 for soldering or the like. Sensor 220 may further be coated with a hydrophilic or hydrophobic layer (not shown) for increasing the biocompatibility of sensor 220.

Wires (not shown) may be welded, soldered, ball bonded, epoxied, etc. to each bonding pad 202, 204 and microprobe sensor 220 may then be placed within elongate body 210 (see FIG. 1). A waterproof epoxy may be used to hold microprobe sensor 220 in place within elongate body 210 and to protect microprobe sensor 220.

3. Method of Using Thermal Conductivity Probe

With reference to FIGS. 1-2B, a representative method of using thermal conductivity probe 200, is provided. As seen in FIG. 1, with the first pair of bonding pads 202 electrically connected to power source "PS", and with the second pair of bonding pads 204 electrically connected to multimeter "M", thermal conductivity probe 200 may be used to determine the thermal conductivity of target tissue. The transient time response of heating elements 222a, 222b is dependent on a thermal conductivity of the medium surrounding microprobe sensor 220 and the substrate underlying microprobe sensor 220.

According to a method of the present disclosure, a 5V output, generated by power source "PS", is used to provide a constant current through heating elements 222a, 222b. A resistance change of the RTD elements 224a, 224b, due to the transient temperature elevation, is measured by multimeter "M", an impedance analyzer or the like. Computer "C" is used to monitor, record and acquire the data and/or readings generated by microprobe sensor 220.

The transient time response of the RTD elements 224a, 224b depends on the thermal conductivity of the surrounding medium and the substrate. A theoretical analysis of the transient conduction, for a configuration where the heater source is sandwiched between two materials (the substrate and the surrounding medium), shows that the composite thermal conductivity calculated from the temperature versus the logarithm of time response is simply an average of the thermal conductivity of the two materials.

The equation for the calculation is:

$$k = \frac{k_{tissue} + k_{substrate}}{2} = \frac{q''}{2\pi}\left(\frac{dT}{d\ln t}\right)^{-1}$$

$k$ - is the calculated thermal conductivity;

$k_{tissue}$ - is the thermal conductivity of the tested tissue;

$k_{substrate}$ - is the thermal conductivity of the sensor substrate;

$q''$ - is the heat flux produced by heating element;

$T$ - is the temperature; and $t$ - is the time

In use, catheter 210 is inserted into the target tissue "T" and microprobe sensor 220 is activated to determine the thermal conductivity of said target tissue. Thermal conductivity probe 200 is adapted to measure thermal conductance $K_{eff}$ as represented by the following equation, as commonly known in the field:

$$K_{eff} = K\left\{1 + \frac{n[(\rho c)_b \pi r_b^2 \overline{V} \cos\gamma]^2}{\sigma_\Delta K^2}\right\} + q_{met}$$

where:

$K_{eff}$ - is the "effective" tissue conductance which is measured. $K_{eff}$ is the combination of conduction (due to intrinsic thermal conductivity) and convection (due to perfusion);

$K_{tissue}$ - is tissue conductance in the absence of perfusion;

$n$ - is the number of blood vessels;

-continued $p$ - in $(pc)_b$ is the density of blood;

$c$ - in $(pc)_b$ is the specific heat of blood;

$r_b$ - is vessel radius;

$V$ - is the blood flow velocity vector within the vessel;

$\gamma$ - is the relative angle between blood vessel direction and tissue temperature gradient;

$\sigma_\Delta$ - is a shape factor term; and $q_{met}$ - is metabolic heat generation.

S. Weinbaum and L. M. Jiji, "A new simplified equation for the effect of blood flow on local average tissue temperature," ASME J. Biomech. Eng. 107: 131-139, 1985.

4. Electrical Conductivity Probe

Figure 10A:
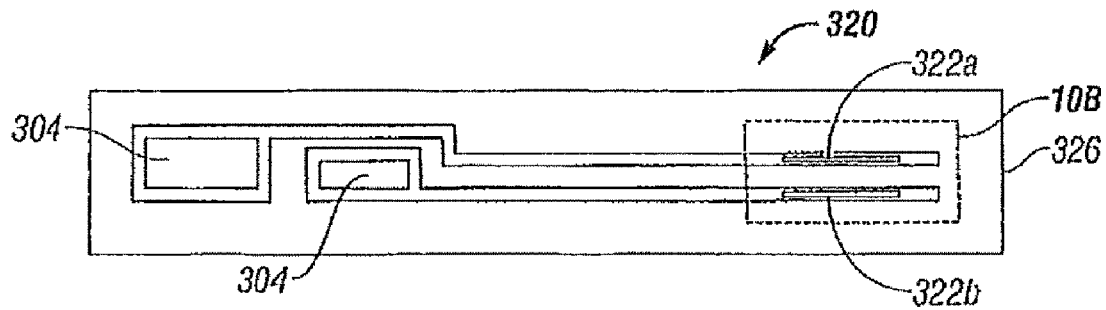
FIG. 10A is a schematic illustration of an embodiment of another electrical microprobe of the sensing system of FIG. 1.
Figure 10B:
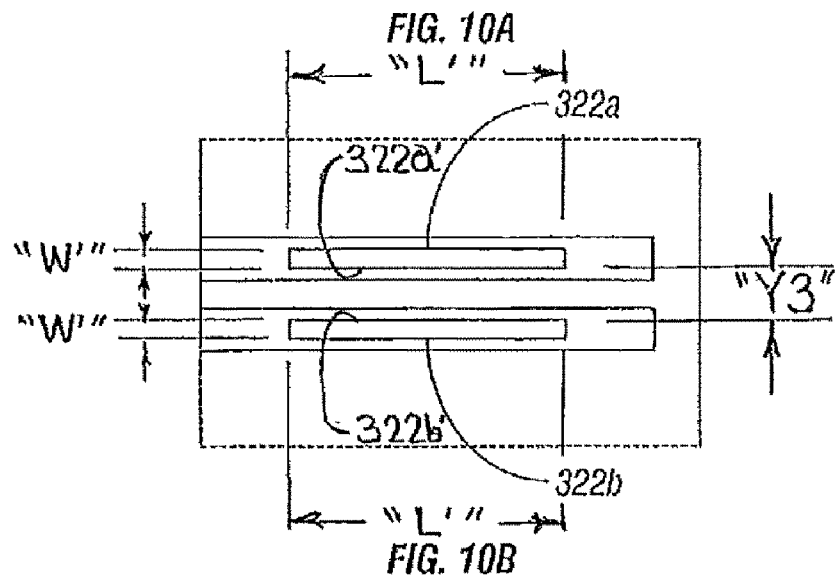
FIG. 10B is an enlarged view of the indicated area of detail of FIG. 10A.

With reference to FIG. 1 and with reference to FIGS. 10A and 10B, a more detailed discussion of electrical conductivity probe 300 is provided. Probe 300 may be in the form of a needle, probe antenna or the like or any suitable configuration. For example, probe 300 may include an elongate body 310, in the form of a catheter, defining a sharpened or pointed distal tip 312.

Probe 300 further includes a sensor 320 suitably secured to catheter 310. Sensor 320 may be disposed at least partially within catheter 310, on an outer surface of catheter 310, imbedded in the outer surface of catheter 310 and/or according to any other suitable.

As seen in FIGS. 10A and 10B, sensor 320 includes a pair of electrodes 322a, 322b defining a sensor area "SA", a pair of electrical leads 323a, 323b respectively connecting electrodes 322a, 322b to bonding pads 304, and a substrate 326 for supporting electrodes 322a, 322b, leads 323a, 323b and bonding pads 304.

In one embodiment, each electrode 322a, 322b has a width "W3" of approximately 150 µm and a length "L3" of approximately 2,000 µm. While the dimensions disclosed herein are representative or exemplary, it is envisioned and within the scope of the present disclosure for the dimensions to have any suitable value, such as, for example, having lengths that are approximately 3.0 times greater than the lengths specified or having lengths that are approximately 0.2 times less than the lengths specified. It is contemplated that the lengths selected, for example, may be chosen for optimal use in a specific target tissue, e.g., liver, lung, kidney, muscle, etc. As best seen in FIGS. 10A and 10B, electrodes 322a, 322b are substantially parallel to one another and are spaced a distance "Y3" from one another. Distance "Y3" may be approximately 300 µm.

Figure 11:
FIGS. 11-16 are schematic illustrations of exemplary steps in the fabrication of the electrical microprobe of FIG. 10.
Figure 12:
Figure 13:
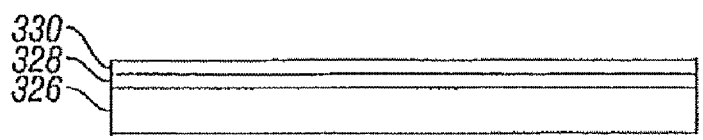

Turning now to FIGS. 11-16, an exemplary method of manufacturing sensor 320 is shown and described. The steps involved in the manufacture of sensor 320 include, as seen in FIG. 11, providing a substrate 326, e.g., a polyimide or other suitable substrate that is inert. In an embodiment, substrate 326 may have a thickness between approximately 300 µm and 1,000 µm, and in a further embodiment may be approximately 500 µm. Next, as seen in FIG. 12, an adhesive layer 328 is deposited on substrate 326 using suitable deposition by evaporation techniques or other suitable deposition and/or evaporation techniques. Adhesive layer 328 may be fabricated from titanium (Ti) titanium tungsten (TiW), platinum (Pt) or other like materials, and may have a thickness of approximately 30 nm. Next, as seen in FIG. 13, a conductive layer 330 is deposited on adhesive layer 228 using suitable deposition by evaporation techniques or other suitable deposition and/or evaporation techniques. Conductive layer 330 may be fabricated from gold (Au), iridium (Ir), platinum-iridium alloy (Pt—Ir) or other like materials, and may have a thickness of approximately 300 nm. The dimensions of microprobe sensor 320 provided herein are merely representative, and may be made larger or smaller depending on the application.

Figure 14:
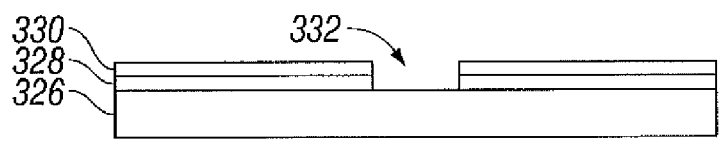
Figure 15:
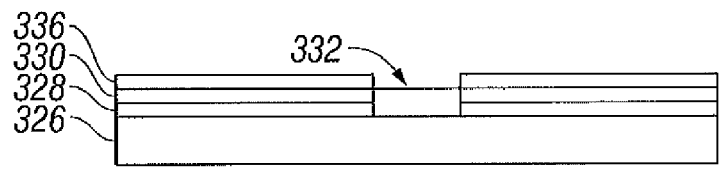
Figure 16:
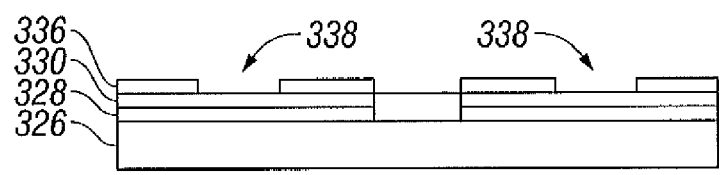
Figure 17:
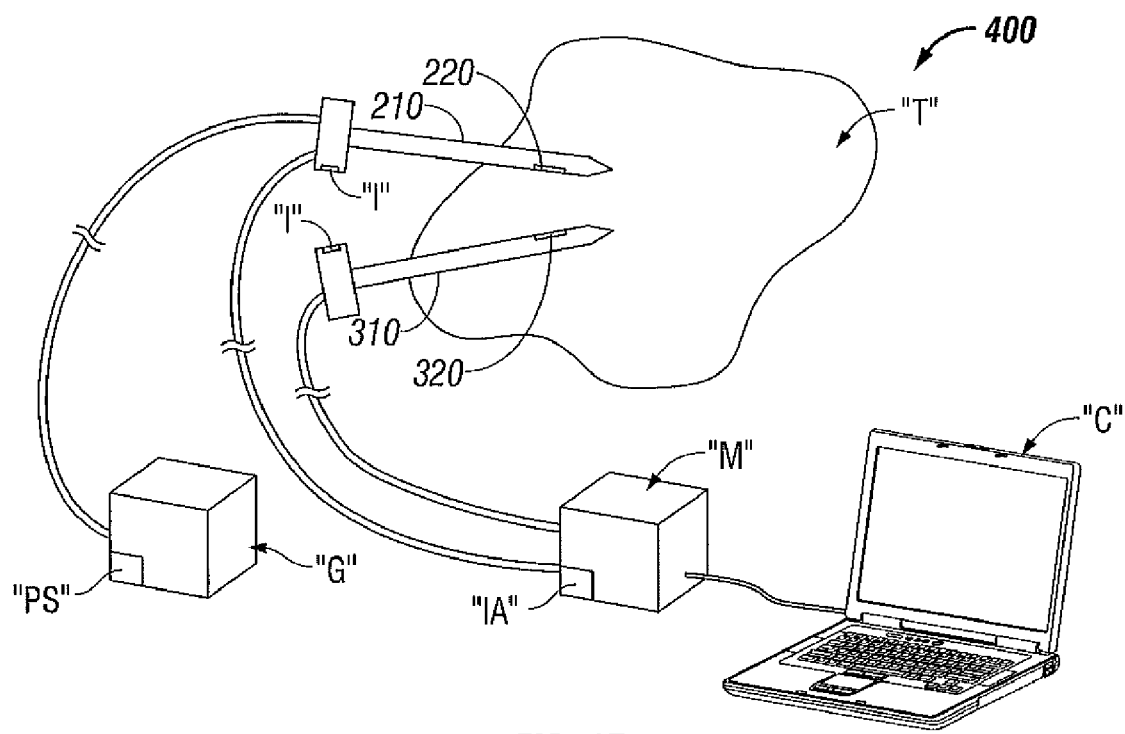
FIG. 17 is a schematic illustration of an electrosurgical system including the sensing system of FIG. 1, shown in operative association with a target tissue.
Figure 18:
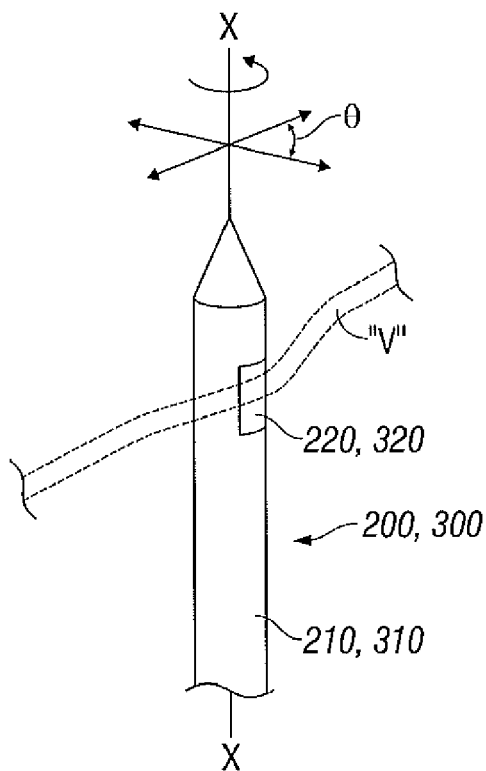
FIG. 18 is a perspective view of a distal end of an electrical microprobe of the present disclosure.

As seen in FIG. 14, suitable photolithography and/or etching techniques are used to generate a desired pattern 332 defining first and second electrodes 322a, 322b. Next, as seen in FIG. 15, an insulating layer 336 is deposited, e.g., spun onto, overtop conductive layer 330 and pattern 332. Insulating layer 336 may comprise a dielectric layer of benzocyclobutane (BCB), silica ($SiO_2$), parylene C or other like materials. Insulating layer 336 functions to protect conductive layer 330 from corrosive element in tissue, such as, for example, saline. As seen in FIG. 16, areas 338 are patterned into insulating layer 336 to define first and second electrodes 322a, 322b and bonding pads 304 and to expose bonding pads 304 for soldering or the like.

Wires (not shown) may be welded, soldered, ball bonded, epoxied, etc. to each bonding pad 304 and sensor 320 may then be paced within elongate body 310 (see FIG. 1). A waterproof epoxy may be used to hold sensor 320 in place within elongate body 310 and to protect sensor 320. Sensor 320 may further be coated with a hydrophilic or hydrophobic layer (not shown) for increasing the biocompatibility of sensor 320.

5. Method of Using Electrical Conductivity Probe

With reference to FIGS. 1, 10A and 10B, a representative method of using electrical conductivity probe 300, is provided. As seen in FIG. 1, with the pair of bonding pads 304 electrically connected to multimeter "M" or impedance analyzer, electrical conductivity probe 300 may be used to determine the electrical conductivity of target tissue prior to an electrosurgical procedure.

According to a method of the present disclosure, a 500 kHz output frequency, generated by multimeter "M", is used to provide electrosurgical energy to electrodes 322a, 322b. A return pad or electrode (not shown) is employed to complete a circuit with electrodes 322a, 322b, via tissue "T". The computer "C" is used to monitor, record and acquire the data and/or readings generated by sensor 320.

Before use, the impedance values by the micro electrical probe are calibrated in different salinity levels against the standard four-electrode probe which provides a direct measure of the electrical conductivity. A calibration curve is generated that relate the impedance value given by the micro electrical probe to the electrical conductivity measured by the standard four-electrode probe at different salinity levels. The electrical conductivity can be calculated by comparing the impedance value with the calibration curve. In use, catheter 310 is inserted into the target tissue "T" and sensor 320 is activated to determine the electrical conductivity of said target tissue "T".

Figure 19:
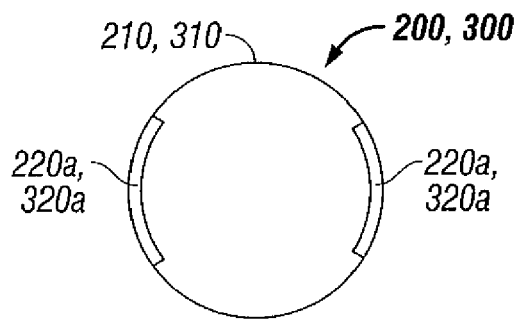
FIG. 19 is a transverse, cross-sectional view of an electrical microprobe as taken through 19-19 of FIG. 1.
Figure 20:
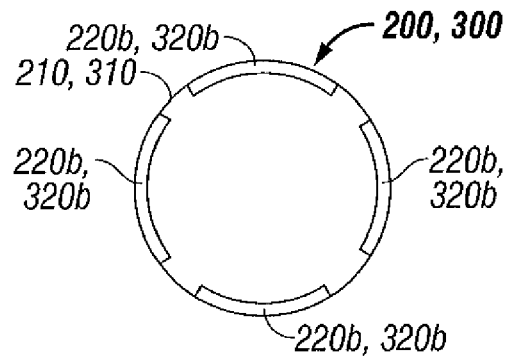
FIG. 20 is a transverse, cross-sectional view of another electrical microprobe as taken through 19-19 of FIG. 1.

While each of the above embodiments illustrates a single sensor 220, 320 associated with each respective device 200, 300, in accordance with the present disclosure, devices 200, 300 may employ or include at least two or multiple sensors 220, 320 disposed around a circumference thereof. As seen in FIG. 19, each of devices 200, 300 may include a pair of sensors 220a, 320a disposed on opposed sides thereof, or as seen in FIG. 20, each of devices 200, 300 may include a sensors 220b, 320b disposed at 90° angles relative to one another.

Figure 21:
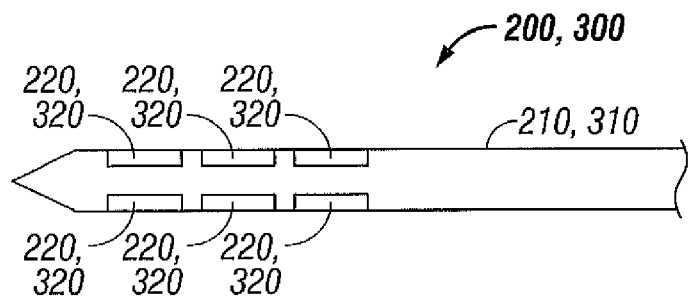
FIG. 21 is a schematic illustration of a distal end of an electrical microprobe according to yet another embodiment of the present disclosure.
Figure 22:
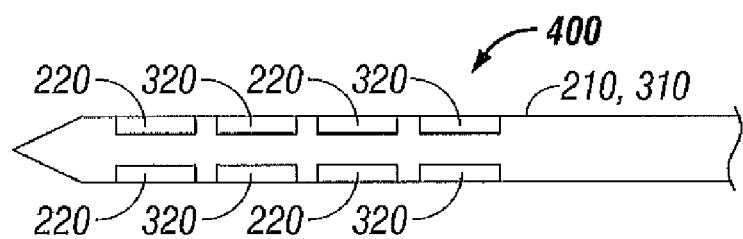
FIG. 22 is a schematic illustration of a distal end of an integrated electrical and thermal microprobe according to still another embodiment of the present disclosure.

As seen in FIG. 21, sensors 220, 320 may be disposed at different axial locations along a length of respective catheter 210, 310. As seen in FIG. 22, sensors 220, 320 may be provided on a single electrosurgical device 400. In this manner, electrosurgical device 400 will be capable of measuring and/or capturing both the values of thermal conductivity and electrical conductivity of target tissue "T".

According to an alternate embodiment of the present disclosure, as seen in FIG. 22, sensors 220, 320 may be incorporated into or otherwise associated with a thermal treatment device 500, in the form of an ablation needle, probe, antenna or the like. Thermal treatment device 500 defines an electrically exposed distal tip 502 configured and adapted to deliver therapeutic energy to target tissue, according to any suitable known method in the art. Distal tip 502 extends from an insulated shaft 504 or the like.

Figure 23:
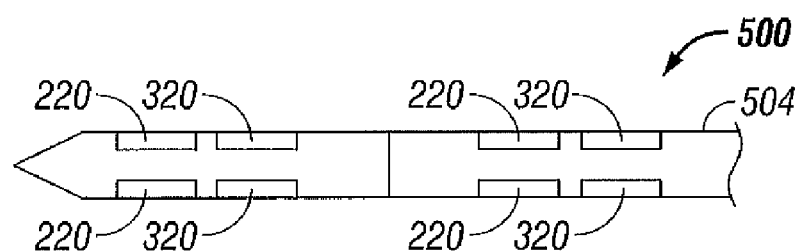
FIG. 23 is a schematic illustration of a distal end of an electrical ablation device according to an embodiment of the present disclosure.

As seen in FIG. 23, sensors 220, 320 may be provided along and/or incorporated into distal tip 502 and/or provided along and/or incorporated into shaft 504. The particular arrangement, location and orientation of sensors 220, 320 relative to one another and relative to distal tip 502 and 504 may be selected or chosen as needed and/or desired.

Figure 24:
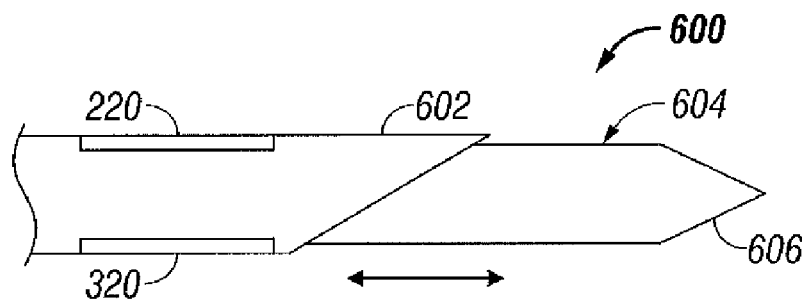
FIG. 24 is a schematic illustration of a distal end of an electrosurgical device according to another embodiment of the present disclosure.
Figure 25:
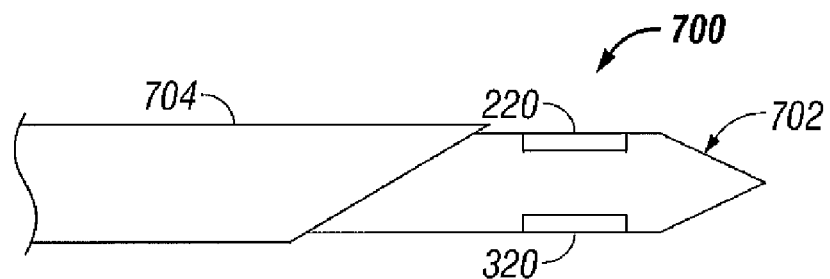
FIG. 25 is a schematic illustration of a distal end of an electrosurgical device according to still another embodiment of the present disclosure.

As seen in FIG. 24, sensors 220, 320 may be provided along and/or incorporated into an outer tube 602 of a thermal treatment device 600. In this manner, outer tube 602 of thermal treatment device 600 may be retracted relative to shaft 604, or in the alternative, shaft 604 may be extended relative to outer tube 602, to expose an operational end 606 of thermal treatment device 600. In an alternate embodiment, as seen in FIG. 25, sensors 220, 320 may be provided along and/or incorporated into a shaft 702 of a thermal treatment device 700. In this manner, shaft 702 of thermal treatment device 700 may be extended relative to an operational outer tube 704, thereby exposing sensors 220, 320. In a further embodiment, operational outer tube 704 may be replaced with an energy delivery needle or the like for delivering therapeutic energy to surrounding tissue and thermal treatment device 700 may be extended relative to energy delivery needle 704.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A system for sensing attributes of tissue, the system comprising:
   a thermal conductivity probe including a sensor configured to measure a thermal conductivity in the target tissue in at least one direction;
   an electrical conductivity probe including a sensor configured to measure an electrical conductivity in the target tissue in at least one direction;
   a power supply operatively coupled to the thermal conductivity probe and configured to supply power to the thermal conductivity probe;
   a multimeter operatively coupled to at least one of the thermal conductivity probe and the electrical conductivity probe, the multimeter configured to deliver energy to at least one of the thermal conductivity probe and the electrical conductivity probe;
   a computer operatively coupled to at least one of the power supply, the multimeter and an impedance analyzer; and
   a substrate,
   wherein the sensor of the electrical conductivity probe includes electrodes that are disposed on the substrate substantially parallel to one another, the electrodes having a width dimension ranging from approximately 30 microns (μm) to approximately 450 microns (μm) and having a length dimension ranging from approximately 400 microns (μm) to approximately 6000 microns (μm).

2. The system of claim 1, wherein the thermal conductivity probe and the electrical conductivity probe are integrated into a single probe.

3. The system of claim 1, wherein the impedance analyzer is operably coupled to the electrical conductivity probe.

4. The system of claim 1, wherein the electrodes have a width dimension of approximately 150 microns (μm) and a length dimension of approximately 2000 microns (μm).

5. The system of claim 1, wherein the electrodes are spaced on the substrate approximately 300 microns (μm) from one another.

6. A thermal conductivity probe for sensing directional attributes of tissue, the probe comprising:
   a body; and
   a sensor operably coupled to the body, wherein the sensor includes:
      a substrate defining a first lateral edge and a second lateral edge;
      a line heater including at least first and second resistive heating elements that are substantially parallel to one another;
      a detector including at least first and second temperature detector; and
      the substrate for supporting the line heater and the detector,
      wherein the at least first and second resistive heating elements and the at least first and second temperature detector are disposed on the substrate,
      wherein the at least first and second resistive heating elements are disposed between the at least first and second temperature detector,
      wherein the at least first and second resistive heating elements define a first length dimension characterizing a length of the at least first and second resistive heating elements on the substrate that is greater than a second length dimension defined by the first and second resistance temperature detectors along a length of the substrate, and
      wherein the substrate provides a thermal conductivity contrast.

7. The probe of claim 6, wherein the body defines a catheter configured for insertion into tissue.

8. The probe of claim 6, wherein the at least first and second resistive heating elements define a first width dimension characterizing a combined width of the at least first and second resistive heating elements on the substrate that is less than a second width dimension defined by the distance between the first and second lateral edges defined by the substrate.

9. The probe of claim 8, wherein the at least first and second resistive heating elements are substantially parallel to one another, wherein the first width dimension ranges from approximately 20 microns (μm) to approximately 300 microns (μm).

10. The probe of claim 9, wherein the first width dimension is approximately 100 microns (μm).

11. The probe of claim 8,
    wherein the at least one first and second temperature detector are disposed on the substrate substantially parallel to one another and each define an inner edge along the length of the substrate, wherein the first and second resistive heating elements are disposed on the substrate substantially parallel to one another and each define an outer edge along the length of the substrate, wherein the distance between the outer edge of the at least first resistive heating element and the inner edge of the at least first temperature detector and the distance between the outer edge of the at least second resistive heating element and the inner edge of the at least second temperature detector each define a third width dimension.

12. The probe of claim 11, wherein the third width dimension is approximately 50 microns (μm).

13. The probe of claim 6, further including an array of sensors.

14. The probe of claim 6, wherein the first length dimension ranges from approximately 1000 microns (μm) to approximately 15,000 microns (μm) and wherein the second length dimension ranges from approximately 300 microns (μm) to approximately 4500 microns (μm).

15. The probe of claim 14, wherein the first length dimension is approximately 5000 microns (μm) and the second length dimension is approximately 1500 microns (μm).

16. The probe of claim 6, wherein the at least first and second temperature detector are each disposed separately in an outer position with respect to the first and second lateral edges defined by the substrate as compared to the at least first and second resistive heating elements, the at least first and second resistive heating elements each disposed separately in an inner position as compared to the at least first and second temperature detector and with respect to the first and second lateral edges defined by the substrate, respectively.

* * * * *